US006877377B2

(12) United States Patent
Dittrich et al.

(10) Patent No.: US 6,877,377 B2
(45) Date of Patent: Apr. 12, 2005

(54) NON-DESTRUCTIVE ULTRASOUND TEST METHOD FOR DETECTION OF DAMAGE AND DEVICE FOR CARRYING OUT SAME

(75) Inventors: Kay Dittrich, Hoehenkirchen (DE); Klaus-Peter Kress, Brunnthal (DE)

(73) Assignee: EADS Deutschland GmbH, Ottobrunn (DE)

( * ) Notice: Subject to any disclaimer, the term of this patent is extended or adjusted under 35 U.S.C. 154(b) by 0 days.

(21) Appl. No.: 10/477,454

(22) PCT Filed: May 4, 2002

(86) PCT No.: PCT/DE02/01617

§ 371 (c)(1),
(2), (4) Date: Jun. 7, 2004

(87) PCT Pub. No.: WO02/093156

PCT Pub. Date: Nov. 21, 2002

(65) Prior Publication Data

US 2004/0231423 A1 Nov. 25, 2004

(30) Foreign Application Priority Data

May 12, 2001 (DE) .......................................... 101 23 237

(51) Int. Cl.[7] .............................................. G01N 29/04
(52) U.S. Cl. ....................................................... 73/602
(58) Field of Search .......................... 73/602, 597, 598, 73/599, 600, 579

(56) References Cited

U.S. PATENT DOCUMENTS

| 4,041,774 A | 8/1977 | Morris et al. ................. 73/67.9 |
| 4,803,638 A | 2/1989 | Nottingham et al. ........ 364/507 |
| 4,953,405 A * | 9/1990 | Hara et al. ..................... 73/602 |
| 5,631,424 A | 5/1997 | Nieters et al. ................. 73/598 |
| 6,028,547 A | 2/2000 | Dory ............................. 342/22 |

FOREIGN PATENT DOCUMENTS

| DE | 195 30 150 A1 | 8/1995 | |
| JP | 62082350 A * | 4/1987 | .......... G01N/29/04 |

OTHER PUBLICATIONS

"Qualification and Validation of New SAPHIR—UT—Technology", R. Heumueller et al; First European Conference on Nondestructive Testing; Copenhagen, May 26–29, 1998, pp. 1–8.

"Diffration coefficients for flat–bottomed holes from 3–D finite difference calculations" J.A.G. Temple, Ultrasonics 1993, vol. 31, No. 1, pp. 3–12.

* cited by examiner

Primary Examiner—Hezron Williams
Assistant Examiner—Rose M. Miller
(74) Attorney, Agent, or Firm—Crowell & Moring LLP

(57) ABSTRACT

In a nondestructive ultrasonic testing method for an implementation in a testing device, defects are installed in a testing area of a structural part by determining reflections on inhomogeneities in a testing area of the structural part. At least one ultrasonic transmitter is provided for coupling ultrasonic excitations into the structural part, and at least two ultrasonic receivers are installed for receiving structure responses to the excitations coupled into the structure. A number of testing points are determined and for each testing point and each location of the ultrasonic receivers, expectancy range data are determined and stored for signal forms being implemented in the testing device. When, an inhomogeneity is present in the respective testing point, excitations are reflected thereon and are measured by the respective ultrasonic receiver. The received reflection data are compared with the stored expectancy ranges to determine the location of a defect.

4 Claims, 2 Drawing Sheets

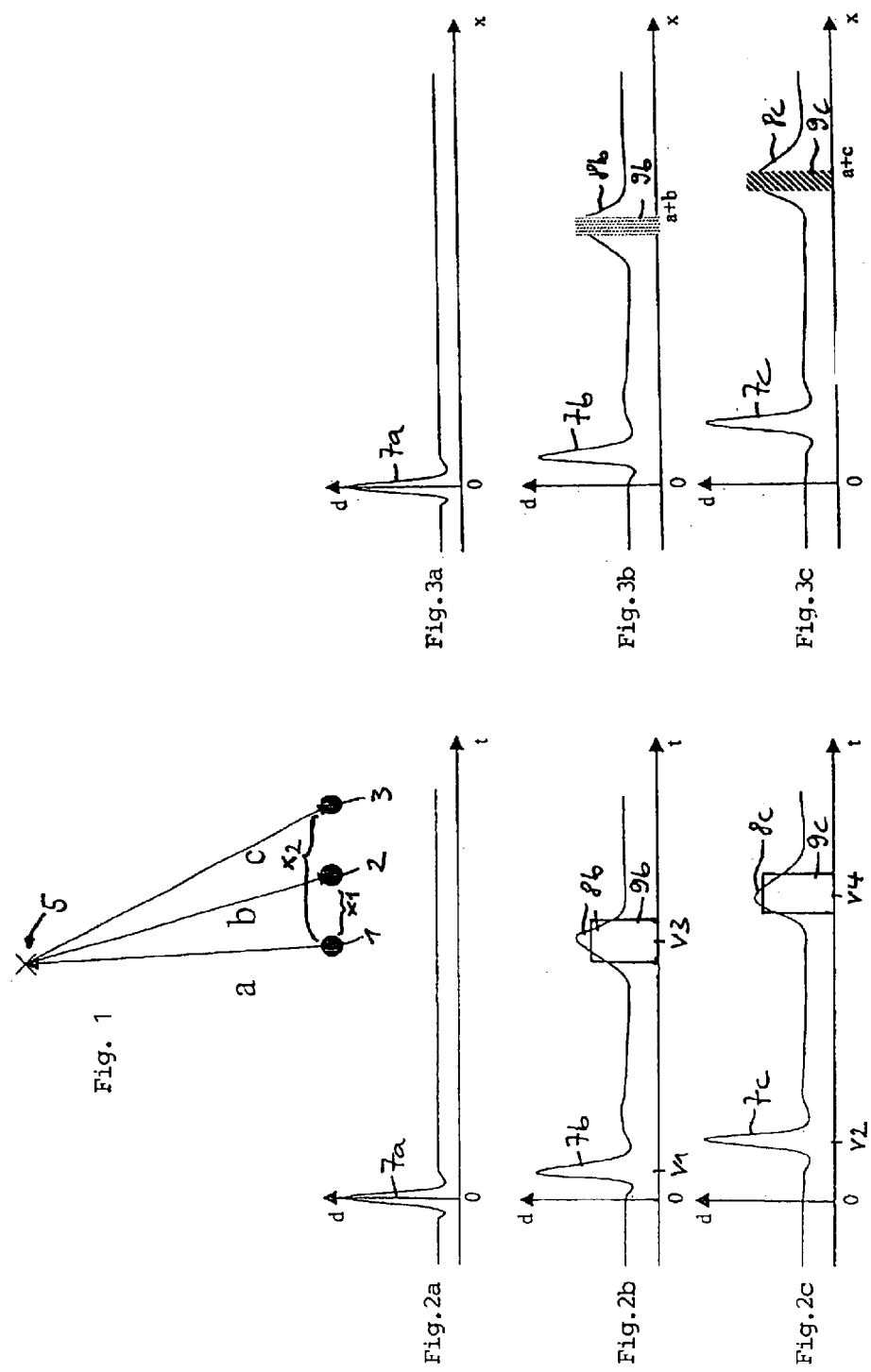

NON-DESTRUCTIVE ULTRASOUND TEST METHOD FOR DETECTION OF DAMAGE AND DEVICE FOR CARRYING OUT SAME

BACKGROUND AND SUMMARY OF THE INVENTION

This application claims the priority of German patent document 101 23 2373, filed May 12, 2001 (PCT International Application No.: PCT/DE02/01617, filed 4 May 2002), the disclosure of which is expressly incorporated by reference herein.

The invention relates to a nondestructive ultrasonic testing method and apparatus for detecting, assessing and localizing defects, with respect to a test region of a structural part.

According to the present state of the art, nondestructive testing methods are used to detect an incipient defect or to follow a developing defect of structures or structural parts, for example, in a vehicle such as an airplane (that is, for checking its structural integrity). In order to check the integrity of structures or structural parts, even when using nondestructive testing methods according to the state of the art, it may be necessary to disassemble the structure or structural parts to be checked, so that they can be made accessible for testing by the testing device. However, such disassembly requires considerable expenditures of time and resources.

From the lecture "Qualification and Validation of New Saphir-UT-Technology" at the 1st European Conference on Nondestructive Testing from May 26 to 29, 1998 in Copenhagen, a nondestructive ultrasonic testing method is known in which highly efficient eddy-current or ultrasonic sensors are temporarily coupled to the component surface. (The most efficient ultrasonic sensor types include, among others, so-called ultrasonic group radiators which have several jointly operated ultrasound sources, preferably in the form of piezoelectric elements). An ultrasonic excitation of the structure emanates from the ultrasound sources, which are controlled by way of an electric excitation. The ultrasonic excitation propagates as a structure response or sound field through the structural component to be tested and is partially reflected by inhomogeneities that may exist in the structure. The sound field reflected at such inhomogeneities can be received by sensors assigned to the ultrasonic group radiators, and converted to an electric signal in order to detect these inhomogeneities in the structure. In this case, the excitation takes place such that the sound field emanating from the group radiator has the shape of a lobe and thus has a preferred direction. The lobe can be focused at a variable distance. In this manner, inhomogeneities can be imaged in a location-resolving image.

This known imaging ultrasound method has the disadvantage that it is very costly in terms of equipment-related expenditures. The number of ultrasound sources that is necessary depends on the required resolution and range; it may comprise 8, 16, 32 or more channels which must be operated simultaneously. For this purpose, a high-expenditure high-frequency electronic system is required for each channel, such as an electronic system for changing between the transmitting and receiving operation; an electronic amplifier system on the controlling and receiving side; an electronic filtering system; a high-frequency analog-to-digital converter of a high bit resolution; as well as a high-expenditure electronic control system in order to achieve a swivelling and focusing of the sound field by a phase-shifted and amplitude-modulated control.

Another disadvantage of the method according to the state of the art is that the quality of the image, in addition to physical parameters (wavelength, ultrasonic wave velocity in the material, damping in the material, etc.), also depends on precise positioning of the sensors. This is particularly uncertain at locations of the structure which are difficult to access by means of radiators and sensors, so that the shape of the structure impairs the precision of the method. As a result, an exact comparison cannot be made between two test results (ultrasonic images) because the positioning generally varies between two tests.

In addition, specifically at those locations which are difficult to access, it is required to expose the surface of the structural part, which results in very high expenditures.

It is therefore an object of the invention to provide a nondestructive testing method and apparatus for the detection, assessment and localization of defects, which achieves high reliability in the test result, with reduced expenditures.

This and other objects and advantages are achieved by the nondestructive ultrasonic testing method and apparatus according to the invention which are suitable for testing structures, particularly those made of metals or fiber composites as well as mixed forms made of these materials. Depending on the material to be tested, the invention is especially suited for detection of defective points in the structure which are caused by corrosion, deformations, fiber ruptures, cracks or delaminations.

In contrast to the described state of the art, the method according to the invention eliminates the need for a focusing and a phase shift of the electronic excitation of the structure to be tested by means of an ultrasound source. The corresponding electronic expenditures are thus eliminated, so that the invention permits an imaging ultrasonic testing at considerably lower expenditures than according to known methods.

Furthermore, permanent application of the ultrasonic elements (that is, of the transmitters and receivers, provided according to the invention) achieves improved coupling of the ultrasonic excitation into the material, increasing their range in comparison to the state of the art. Such permanent application can be performed, for example, by gluing or soldering, or by a fixing device.

Another advantage of the invention is that the positions of the transmitters and receivers are constant between two time-shifted tests, because these are permanently arranged on the structure. As a result, an exact comparison of the measuring data of different measurements can be carried out.

Other objects, advantages and novel features of the present invention will become apparent from the following detailed description of the invention when considered in conjunction with the accompanying drawings.

BRIEF DESCRIPTION OF THE DRAWINGS

FIG. 1 shows an arrangement of ultrasonic elements with three piezo elements for coupling-in an excitation and receiving the resulting structure response, which arrangement is provided on the structure having the structural area to be tested;

FIG. 2a illustrates the temporal course of the structure excitation coupled from the transmitter 1 into the structure, in the form of an extension time diagram, in which the variable t is entered on the abscissa, and the extension of the structure at the location of the transmitter 1 is entered on the ordinate;

FIG. 2b is an extension-time diagram which shows the temporal course of the structure response measured by a first receiver, as a result of the excitation illustrated in FIG. 2a, in which the variable t is entered on the abscissa and the extension of the structure at the location of the transmitter 1 is entered on the ordinate;

FIG. 2c is an extension-time diagram similar to FIG. 2b, which shows the temporal course of the structure response measured by a second receiver, based on the excitation illustrated in FIG. 2a;

FIG. 3a shows the excitation illustrated in FIG. 2a, transformed into an extension—path diagram, with the extension d entered on the ordinate, and the path x of the extension (which path the structure excitation originating from the transmitter traverses at an assumed propagation velocity in the material) entered on the abscissa;

FIG. 3b is an extension—path diagram similar to FIG. 3a, in which the extension propagating from the excitation illustrated in FIG. 3a is shown at a defined point in time, as a function of the path covered from the site of the excitation and, in addition an expected range is shown;

FIG. 3c is an extension—path diagram similar to FIG. 3a, in which the extension propagating from the excitation illustrated in FIG. 3a is shown at a defined point in time, as a function of the path covered from the site of the excitation and, in addition an expected range is shown;

DETAILED DESCRIPTION OF THE DRAWINGS

Figure 5A:
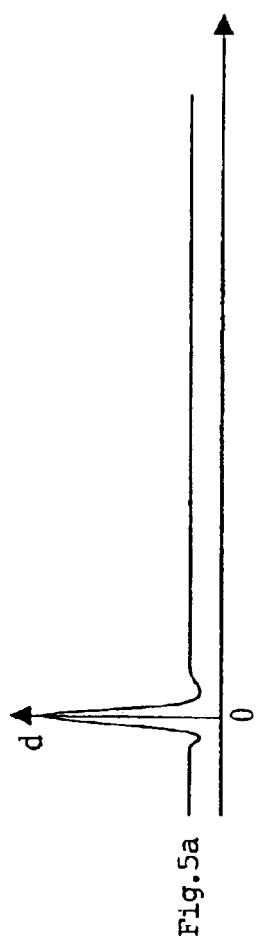
FIG. 5a is a view of the excitation illustrated in FIG. 2a in the form of an extension—path diagram corresponding to FIG. 3a, in which the path x which is traversed by the extensional wave in the structure (at an assumed propagation velocity in the material) is entered on the abscissa.
Figure 5B:
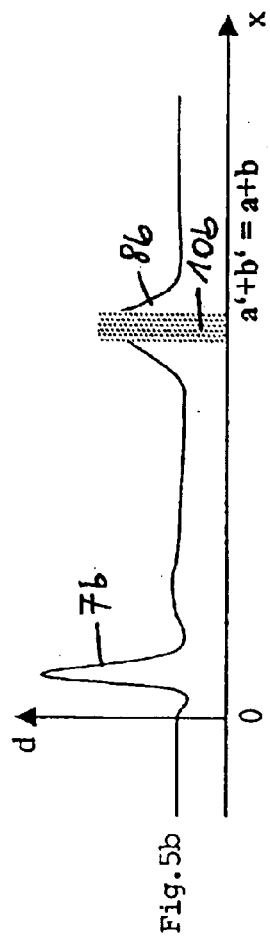
FIG. 5b is an extension—path diagram corresponding to FIG. 3b, with an expected path range for a first receiver, which expected path range corresponds to two different paths for a received sound wave pulse.

For testing an area of a structure for defects, according to the invention at least one ultrasonic transmitter and at least two ultrasonic receivers (preferably constructed as piezo elements) are permanently arranged or installed at predefined positions on the structure, prior to the actual testing of the structural area. In the actual practical applications, the number of the ultrasonic elements to be provided is preferably larger (usually larger than four), in order to achieve a better resolution. The positions of the transmitters and receivers are determined such that they are suitable for detecting the effects of inhomogeneities, by measuring the consequent effects of excitations, existing in the structural area to be tested.

Before implementation of the testing method according to the invention, a calculation is carried out for a number of points in the area of the structure that is to be tested. The calculation determines for each of these testing points, the structure responses (type and temporal course) to an excitation of the structure emanating from a transmitter, which excitation acts upon the installed receivers. For the purpose of such calculations, it is assumed that an inhomogeneity (thus, for example, a defective point) exists at respective structural points. The determined structure responses are therefore structure responses resulting from local ultrasonic waves scattered at the respective testing points.

In a suitable manner, the positions of the testing points are situated in the testing area of the structure, such that a required testing of the structural area can take place in a sufficient fashion. The testing points are preferably regularly spaced over the structural area to be tested. However, the testing points may also form an irregular network in the testing area. The following is taken into account in the calculation of the structure response for each testing point at which an inhomogeneity is assumed to exist: The predetermined positions of the at least one ultrasonic actuator and of the ultrasonic sensors as well as the propagation behavior of the ultrasonic waves in the material (which is supposed to be known or assumed to be known) based on the characteristics of the structure material in the case of a predefined type of excitation signal. On the basis of analytical or empirical methods, the characteristics of the structure material, and thus the propagation behavior of the ultrasonic excitations in the structure when an inhomogeneity is present in one or more testing points, were determined before the implementation of the actual testing method.

According to the invention, the actual testing is performed by measuring the structure responses of the receivers to predefined excitations correlating with the calculations. When a sensor detects a signal whose arrival time or course (based on a comparison with the calculation of the structure responses) allows a conclusion that an inhomogeneity exists in one or more of the observed testing points, these testing points are identified as structural points in which an inhomogeneity of the structure may be present. The locations of inhomogeneities are assigned to the respective location on the structure component in an imaged or other manner. In the case of a visual display of the structure, these points can be visually entered in the visual display in an appropriate manner.

If the signal, which is expected when inhomogeneities are present, is not unambiguous (because several locations exist from which a defined scattering contribution, for example, from an extension—time diagram, could originate) several transmitting—receiving combinations are to be superposed. That is, a correspondingly large number of transmitters and receivers is to be provided. In this case, testing points, at which significant contributions are made in the case of several combinations of used transmitters and receivers, represent structural points at which inhomogeneities actually exist with a high reliability. When comparing the calculation results with the measuring results, additional analyses can therefore be used (for example, comparisons of the calculation and measuring results of different testing points) in order to resolve ambiguities of the results (that is, in order to assign to an individual testing point inhomogeneities, which, because of one of the measurements, may apply to several testing points.

Actual inhomogeneities, that is, inhomogeneities defined by the design of the structure itself, are differentiated from the inhomogeneities to be detected according to the invention (for example, those which are attributable to defects) by means of additional analyses or by a comparison. The comparison preferably takes place by visually comparison. In this case, the inhomogeneities determined by means of the calculations and measurements carried out at the testing points are compared with actual inhomogeneities existing in the testing area, in order to identify additional inhomogeneities at other locations as partial defective points.

The comparison of the calculation results with the measurement results is carried out as follows according to the invention:

When a structure excitation is coupled in by means of an ultrasonic sensor, each ultrasonic receiver measures the signal coupled into the structure by the excitation of the transmitter on the basis of the occurred time-variable structure extension as a function of the time or as a function of equivalent functional quantities, such as locations (in the following marked x), at which the extension is occurring. When an inhomogeneity exists, the receiver receives a structure response to an excitation emanating from a transmitter as the sum of two contributions: A first contribution is formed by the ultrasonic wave which propagates directly from the transmitter to the receiver. A second contribution is formed from scatter contributions of inhomogeneities in the structure to be tested which differ in their temporal course from the first contributions on the basis of an assumed wave propagation between the transmitter of a scattering inhomogeneity and the receiver in the case of the respectively implemented excitation. From these assumptions, an expected range can be determined, for example, with respect to times t or locations x, in which an expected structure response occurs in the form of time-dependent extensions, in the following called d.

In a case in which the excitation is a single pulse, the inhomogeneity existing at a certain testing point can be determined by measuring a signal by a receiver at an expected point in time because the excitation propagates on the basis of the known running time of the signal in the structure while taking into account the reflection as a result of the inhomogeneity in the observed testing point and arrives at the receiver in the expected form.

For this pulse excitation case, the method according to the invention for the identification of structure inhomogeneities is described for the embodiment of an arrangement of ultrasonic elements schematically illustrated in FIG. 1:

For the coupling-in of an excitation and for receiving the resulting structure response, three piezo elements 1, 2, 3 are arranged on the structure with the structural area to be tested. A first piezo element 1 is provided for coupling the excitation into the structure, and the piezo elements 2, 3 are provided for receiving the structure response. In FIG. 1, the structure has the reference number 4, and a testing point 5 is illustrated as an example, at which the presence of an inhomogeneity is examined. The transmitter piezo element 1 excites the structure by means of a pulse at the point in time t=0. The excitation reaches the receiver 2, among others, via the path x1 and reaches the receiver 3 via the path x2. If an inhomogeneity is present at the structural point 5, the excitation arrives, in addition, by reflection at the structural point 5, via the paths a and b at the receiver 2 and, via the paths a and c, at the receiver 3. The temporal course of the excitation is schematically illustrated in FIG. 2a, and the temporal course of the structure responses received by the receiver piezo elements 2, 3 is schematically illustrated in FIGS. 2b and 2c. The curves in FIGS. 2a, 2b, 2c are extension—time diagrams in which the time t is entered on the abscissa, and, in a simplified manner, the amount of the extension or deflection of the structure at the location of the respective piezo element 1, 2, and 3 respectively is entered on the ordinate (the extension at a given frequency is generally defined by its magnitude and phase).

As a result of the excitation by the transmitter element 1, an ultrasonic wave front 7a is generated (FIG. 2a). In the case of the arrangement of FIG. 1, the measuring of the subsequent structure response is carried out at the local receivers or sensors 2 and 3. The ultrasonic wave front 7a emanating from the element 1 first reaches the first receiver 2 on the direct path x1 with a first time delay v1 relative to the excitation at t=0, as illustrated by the extension 7b of the structure measured by the receiver 2 (FIG. 2b). After a delay v2 (in comparison, once again to the time of the excitation at t=0), the wave front reaches the second sensor 3 which measures an extension 7c (FIG. 2c). In addition to the direct signals, in the case of an assumed inhomogeneity in the structural point 5, the sensors 2 and 3, in the case of an assumed inhomogeneity in the structural point 5, receive ultrasonic signals based on structure extensions which have arisen indirectly by way of a scattering at the testing point 5 because, at the structural point 5, a part of the wave coupled in by the transmitter 1 is scattered in the direction of the receivers 2 and 3. As a result, ultrasonic signals attributable to extensions 8b and 8c will be measured with the time delays v3 and v4 respectively by the receivers 2 and 3 respectively.

If the assumed parameters (dispersion behavior, ambient parameters, etc.) are otherwise constant the delay or the point in time at which the scattered wave arrives at the receiver 2 and 3 respectively, is a function of the position of the testing point 5 in relation to the transmitter 1 and the receivers 2 and 3.

In FIGS. 3a, 3b and 3c, the extension courses of FIGS. 2a, 2b and 2c were transformed into respective extension—run distance or extension path diagrams, in which the run distance is entered on the abscissa by means of the letter x. In the case of a constant propagation velocity in the structure to be tested, this can take place directly by means of the formula t=x/c. In the case of structures with a more complex dispersion behavior of the material, corresponding different transformations are to be used which should be determined beforehand according to the invention.

When an inhomogeneity is present at the structural point 5, the receivers 2 and 3 receive extensions 8b, 8c after the excitation has run through the distance a+b and a+c respectively (FIGS. 3b and 3c respectively). When examining a testing point 5 for structural inhomogeneity existing there, according to the invention, expectancy ranges 9b (FIG. 3b) and 9c (FIG. 3c) are provided, within which an extension occurs at the receivers 2 and 3 respectively due to a reflection at the testing point 5. (These expectancy ranges are determined experimentally or preferably analytically before the measuring is carried out.) When it is determined by the receivers 2 or 3 that an extension occurs within an expectancy range, an inhomogeneity is determined to exist at the testing point 5. The expectancy ranges are preferably predetermined as a function of the time, or the arrival of the increase is examined as a function of the time.

According to the invention, this approach is carried out at a plurality of testing points 5, which are to be determined such that a sufficient examination of the structural part (and, if required, a sufficient visual representation of inhomogeneities) can take place. The testing points are preferably distributed over the structural area to be tested.

Figure 4:
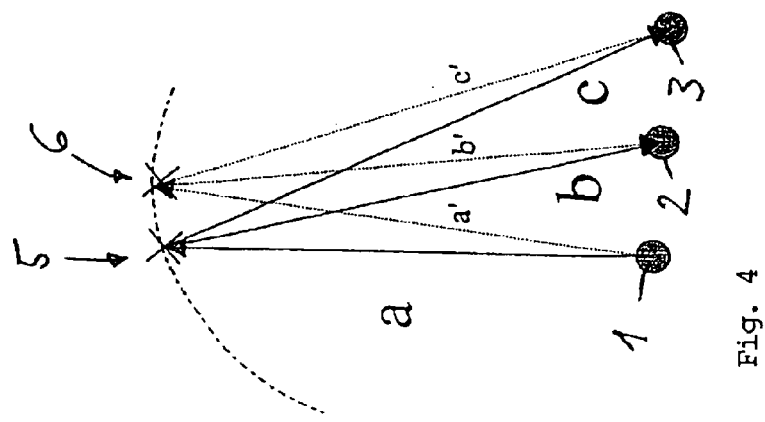
FIG. 4 is a representation of geometric relationships in the case of the transmitter—receiver arrangement according to FIG. 1, for explaining the method according to the invention.

As illustrated in FIG. 4, the assignment of an inhomogeneity to a particular testing point does not have to be unambiguous for an individual transmitter-receiver pan. In the following explanation, the identification of the relevant testing points with inhomogeneities will be described by means of FIG. 4 and FIGS. 5a, 5b, 5c for the case of ambiguities of the measurements.

As shown in FIG. 4, an inhomogeneity situated in a testing point 5 or a testing point 6 which differs therefrom, can both lead to the same signal measured by a receiver 2, if the run distance also amounts to a+b. In the case of a transmitter-receiver constellation according to FIG. 4, this applies to testing points which are situated on an ellipse through the testing point 5 or 6 with the positions of the transmitter and of the receiver 2 as focal points, as is illustrated in the extension—path distance diagram of FIG. 5b. The sound wave pulse 8b received by the receiver or sensor 2 is situated within the expectancy range 10b. In this case, according to the invention, the expectancy range had been determined before the measurement on the basis of testing points 5 and 6 (FIG. 4) with the above-mentioned assumptions. Since the path of the sound wave (a+b) reflected at the testing point 5 is of the same length as that of path (a'+b') of the sound wave reflected at the testing point 6, the same expectancy range 10b is obtained in the extension—path distance diagram of FIG. 5b for both testing points 5 and 6. That is, the two expectancy ranges are situated at the same location of the path distance x (abscissa).

Figure 5C:
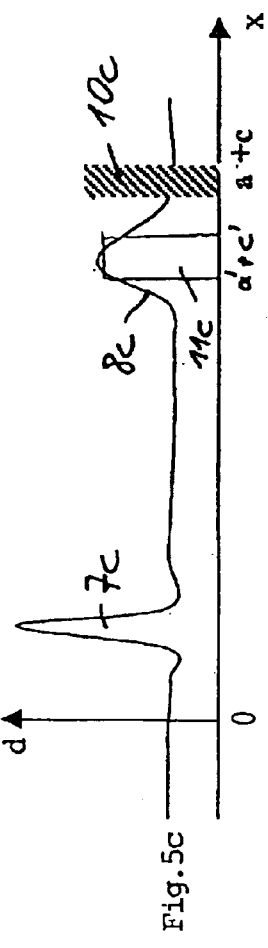
FIG. 5c is an extension—path diagram corresponding to FIG. 3c with an expected path range for a second receiver, which expected path range does not correspond to the path for a sound wave pulse reflected at the observed testing point, so that a decision can be made therefrom concerning the relevant testing point from the two testing points possible according to the measurement of FIG. 5b.

FIG. 5c illustrates the extension—path distance diagram for the second receiver 3. The sound wave pulse 8c reflected on an inhomogeneity at the testing point 6 and received by the receiver 6 has covered the path (a'+c). Correspondingly, the received sound wave pulse 8c occurs in the diagram of FIG. 5c at the path distance (a'+c') of the abscissa. When looking at testing points 5 and 6, two different expectancy ranges 10c and 11c respectively are obtained for the receiver 3 for a sound wave pulse reflected at these testing points 5 and 6 because, as a result of a reflection at testing point 5, the path distance (a+c) would occur which would correspond to the expectancy range 10c, and, as a result of a reflection at the testing point 6, the path distance (a'+c') would occur which corresponds to the expectancy range 11c. As a result of the fact that the sound wave pulse 8c measured by the receiver 3 in the path distance diagram of FIG. 5c is situated in the same path distance area (abscissa) as the expectancy range 11c, the measured sound wave pulse 8c has arrived at the receiver 3 because of the reflection of the excitation on the testing point 6.

Generally, when ambiguities of measurements exist with respect to several measuring points, according to the invention, the expectancy ranges or expected run distances of all relevant testing points for the position of each receiver are compared with the measuring signals received by the respective receiver.

Thus, according to invention, by comparing structure responses measured by sensors installed on the structure with the area to be tested, to excitations with expectancy ranges determined with respect to defined testing points, conclusions are drawn with respect to inhomogeneities at the location of the defined testing points. The determined inhomogeneities are preferably visually indicated by means of an imaging process for further analysis. For example, an automatic crack pattern detection is considered in this case. The image analysis as part of the result analysis can take place in a data processing unit that is connected with the sensors, for example in a wireless manner. Additional parts of the result analysis can also be performed there.

In addition to physical parameters, the local resolution of the I imaging method depends also on the fineness of a grid selected for the testing points. Depending on the signal-to-noise ratio of the measured data, mathematical resolution can definitely be one or more orders of magnitude higher than indicated by the space cell which can be resolved by the maximal sampling rate, as long as the measuring points are sufficiently coherent and synchronous with the excitation.

If a sufficient number of combinations of transmitters and receivers are available, by means of a corresponding superposition (for example, summation), on the one hand the resulting ambiguity can be reduced and, on the other hand, a distribution of the inhomogeneities over the location for the testing area can be established which indicates how inhomogeneously this location acts with respect to all combinations.

For the purpose of the testing method and apparatus according to the invention, functions of any type can be used as excitations to be coupled into the structural part. Preferably, however, excitation pulses are used.

The method according to the invention and the device according to the invention respectively can be applied to any arrangement of ultrasonic elements which meet the above-indicated physical conditions according to the invention. Because of the generally three-dimensional propagation of the ultrasonic waves, the described method is provided for three-dimensional applications. In many cases, the three-dimensional propagation behavior in thin structures can be described approximately two-dimensionally, or can be projected to a two-dimensional problem. In those cases, this method can also be applied to two-dimensional structures.

Since the invention can produce an ultrasonic image of the structure, the generated data are suitable for additional analytical applications. Thus, particularly in the case of larger structures, distances or geometries (dimensions) can be determined in a precise manner from the ultrasonic image. As a result, a global distance measurement is possible. Applications for the detection and determination of global deformations therefore become possible.

Because of its locating capability, additional diagnostic applications of the method according to the invention are also possible: For example, when the ultrasonic transmission behavior on the boundary layers changes, a conclusion can be drawn with respect to a significant change of the boundary layer (for example, a significantly faulty position of bolts).

In addition to amplitude-related reflection, phase-related and frequency-related scattering of the ultrasonic waves can also be assessed locally in order to increase further the reliability of the diagnosis of defects. However, for this purpose, it is necessary to superimpose the extension values from the respective expectancy ranges not only with respect to magnitude, but also with respect to phase and frequency during the summation (coherent summation). With the assumption of a predetermined phase and frequency behavior during wave propagation along a trajectory, deviations therefrom measured in the expectancy area can be assigned to a local inhomogeneity and are therefore used for a further characterization.

Using an arrangement of ultrasonic elements the method according to the invention can be used in a physically meaningful manner if the following criteria are met at least in relevant partial areas of the structural component to be tested or of the structural part to be tested:
  a. The wavelength of the ultrasound must be comparable to (not more than one magnitude larger) or small in relation to the dimensions of the inhomogeneities in the structural component, which are to be resolved by the imaging method.

b. The ultrasonic excitation and measurement must be local. That is, the local measuring range should be comparable to or small compared to the inhomogeneity to be resolved. If this is not possible or required, the dimension-caused ultrasound characteristics of the coupled sensor must be taken into account in the signal analysis.

c. The wave propagation in the structure has to take place at least in sections approximately according to linear laws of the material.

d. The arrangement of the ultrasonic elements is to be provided such that the geometric difference between transmitter-receiver combinations or the ultrasound field caused by them is high enough to reduce sufficiently the possibility of ambiguity in the above-described method. For example, to achieve a horizontal resolution over a predetermined range also in the horizontal direction, a non-disappearing aperture of the arrangement is required.

e. The time-related resolution of the measurement must be so high that a hypothetically measured reflex in the area to be observed can unambiguously be localized with a required resolution: The remaining time-related lack of definition (for example, time between two samples) must not displace or distort the hypothetical wave propagation more than is permitted by the required resolution.

The above-listed criteria a through e must be met simultaneously; that is, each of the above-mentioned criteria has to be considered to be a necessary condition.

For the construction of the testing device according to the invention, several variants can be used:

Each element capable of locally generating or measuring an ultrasonic wave (condition b.) can be provided as an ultrasonic element. The following can currently be used for generating ultrasonic waves: Piezo ceramics, thermal ultrasound sources (for example, resistive heat sources, laser-generated sources; each with a glass fiber feed line or directed by the atmosphere), field-induced sources, etc. For measurement of ultrasonic waves, the following are examples of currently available devices that can be used: Piezo ceramics, extension sensors (DMA) and fiber-optical Bragg grating sensors. In most cases, the coupling takes place by means of a coupling medium (for example, a bonding agent). As an exception, methods using air coupling or using a laser can also be applied.

According to the invention, the same transmitter and receiver respectively can be used for several transmitter—receiver combinations, so that the electronic expenditures can be maximized. The entire ultrasound image for the analysis will then be obtained from the superposition of the individual measurements. The transmitter and receiver form the actual testing device, while the result analysis, including the signal processing, takes place in an analyzing unit. The functions which must be performed to implement the method according to the invention can be accomplished in different ways with respect to the hardware. The result analysis is preferably carried out in a data processing unit which is connected (by way of lines or in a wireless manner) with the testing device. The sensor drivers can be implemented at the sensors or in the data processing unit.

The ultrasonic elements are in a mutual signal connection, with communication between the individual elements being accomplished via lines or wirelessly.

The ultrasonic sensor system arranged on the structure to be tested can also be supplemented by an additional sensor system, for example, by conventional extension sensors or temperature sensors, in order to further improve or supplement the testing result.

Furthermore, the electronic expenditures can be reduced if, during an individual measurement, one ultrasonic element operates only as a transmitter and another operates only as a receiver. Although information is eliminated which could otherwise be obtained for each individual element in the pulse—echo operation, in return, the electronic expenditures of switching between the transmitting and receiving operation are eliminated. For example, in the case of 16 ultrasonic elements, a total of 16*15=240 possible transmitter—receiver combinations are obtained in which one element operates as a transmitter and one element operates as a receiver.

Furthermore, as a result of the constant positioning of the transmitters and receivers on the structure to be tested, it becomes possible either to increase the range of the ultrasound of the arrangement while the signal-to-noise ratio remains the same, or to improve the signal-to-noise ratio while the range remains the same. This is possible because several measuring results can be superposed, so that noise influences in the measuring circuit or in the ultrasonic wave propagation (for example, acoustic interferences) are averaged out. It is therefore possible, while the quality of the ultrasonic process is the same, to operate with far lower excitation levels (for example, in the range of 1 to 30 V) than in applications according to the state of the art, in which excitation voltages between 50 and 300V are customary.

As a result of the invention, a further electronic system for amplifying the excitation signal can also be eliminated, and simpler electronic modules can be used. Because of the use of lower voltages, electromagnetic interferences are also reduced, so that a permanently installed arrangement according to the invention can also be used in electromagnetically more critical areas (for example, on a flying apparatus).

Another advantage of the method according to the invention is that it is no longer necessary to use only a single defined excitation form. In another embodiment of the invention, an excitation can be built up from a sum of individual excitations if linear material is present in the case of a structure to be tested. A mathematical superposition of individual measurements will then achieve a total result that corresponds approximately to the result which would have been obtained by a summarizing excitation. In this manner, theoretical excitations with extremely high amplitudes can be simulated. If, for example, the transmitters were operated at 100V at a defined signal-to-noise ratio, according to the above-described method, theoretical excitations in the range of from $10^5$–$10^6$ V and more could be simulated, which would not be possible with respect to the application. In the case of the same signal-to-noise ratio, a corresponding range increase is therefore obtained or, when the range is the same, a corresponding signal-to-noise improvement is obtained.

It is an advantage of the invention that, because the ranges are larger than in the method according to the state of the art, the area of the sensor system to be applied can be smaller than in known methods and devices, and is therefore also small in comparison to the dimensions of the structural component. In addition, the weight and the required installation volume can be reduced considerably, so that the sensor and the electronic analyzing system can be housed in a micro-electronic form.

Summarizing, the invention provides a nondestructive ultrasonic testing method for use in a testing device for detecting defects in a testing area of a structural part by determining reflections on inhomogeneities in the testing area. At least one ultrasonic transmitter couples ultrasonic excitations into the structural part and at least two ultrasonic receivers are installed on the structure, for receiving structure responses to the excitations. A number of testing points are determined and stored in the testing area, and for each testing point and each location of the ultrasonic receivers, expectancy ranges for signal forms are implemented in the testing device. When an inhomogeneity is present at a testing point, excitation signals reflected thereon are measured by the respective ultrasonic receiver.

The ultrasonic testing method comprises:

coupling at least one predetermined excitation signal into the structural part; and measuring and storing the structure response by each receiver;

comparing the structure response measured by each receiver for each defined testing point, with the respectively relevant determined expectancy range;

identifying defective sites by comparison of the determined inhomogeneities with structurally defined inhomogeneities.

The receivers carry out the measuring and storage of the structure response either in a temporal sequence or simultaneously, or according to a combination thereof.

When ambiguities of the measured structure responses exist with respect to the assignment of an inhomogeneity to a certain testing point, the expectancy ranges of several considered testing points are compared with the measuring signals received by each receiver. The expectancy ranges may be formed of expected run distances. The identification of defective sites may also take place by a visual comparison.

One transmitter (1) can be provided for coupling the excitation into the structure and at least two receivers (2, 3) can be provided for receiving the structure response.

A testing device is provided for implementing the above-mentioned steps. This testing device may be connected with a data processing unit in which at least a part of the result analysis is carried out.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A nondestructive ultrasonic testing method for the detection of defects in a testing area of a structural part by determining reflections on inhomogeneities in the testing area, said method comprising:

permanently installing on the structure at least one ultrasonic transmitter for coupling ultrasonic excitations into the structural part and at least two ultrasonic receivers for receiving structure responses to the ultrasonic excitations;

identifying a plurality of testing points within a testing area of the structural part;

for each pairing of a particular testing point and a particular location of an ultrasonic receiver, determining and storing an expectancy range for a signal that will be measured by the ultrasonic receiver at the particular location, in response to an ultrasonic excitation coupled into the structural part, when said excitation is reflected by an inhomogeneity at the particular testing point;

coupling at least one predetermined excitation into the structural part;

measuring and storing a structure response at each receiver;

comparing the structure response measured by each receiver with the stored expectancy range for each defined testing point;

imaging the result of the comparison on corresponding geometric site of an ultrasonic image thus built-up successively, which geometric site is part of the respective expectancy range, whereby an identification of defective sites can take place on the ultrasonic image by a comparison of the determined inhomogeneities with structurally defined inhomogeneities; wherein, in the case of the ultrasonic testing method using a linear material, a plurality of predetermined ultrasonic excitations are sequentially coupled into the structural part with measurement and storage of the structure responses being performed by the receivers; and the structure response to a particular excitation measured by each receiver is compared with the expectancy range that is relevant to each particular testing point, determined on the basis of a sum of the sequentially coupled-in ultrasonic excitations.

2. Nondestructive ultrasonic testing method according to claim 1, wherein image analysis methods are used for the visual comparison.

3. The nondestructive ultrasonic testing method according to claim 1, wherein ultrasonic piezo elements are used as the transmitter and/or receivers.

4. The nondestructive ultrasonic testing method according to claim 3, wherein heat pulse or extension sensors are used as ultrasonic piezo elements.

* * * * *